(12) United States Patent
Zhang

(10) Patent No.: US 8,147,412 B2
(45) Date of Patent: Apr. 3, 2012

(54) ULTRASOUND DOPPLER DEALIASING WITHOUT ZERO INSERTION

(75) Inventor: Yu Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1097 days.

(21) Appl. No.: 11/646,835

(22) Filed: Dec. 27, 2006

(65) Prior Publication Data

US 2008/0156106 A1   Jul. 3, 2008

(30) Foreign Application Priority Data

Oct. 13, 2006   (CN) .......................... 2006 1 0063140

(51) Int. Cl.
*A61B 8/00* (2006.01)

(52) U.S. Cl. .......................... 600/455; 600/453; 600/454

(58) Field of Classification Search .................. 600/437, 600/453, 454
See application file for complete search history.

(56) References Cited

U.S. PATENT DOCUMENTS

| | | | |
|---|---|---|---|
| 4,934,373 A | 6/1990 | Angelsen et al. | |
| 4,966,153 A * | 10/1990 | Nakamura et al. | 600/455 |
| 5,183,047 A * | 2/1993 | Burckhardt | 600/455 |
| 5,553,621 A | 9/1996 | Otterson | |
| 5,646,623 A * | 7/1997 | Walters et al. | 342/129 |
| 5,676,148 A * | 10/1997 | Koo et al. | 600/447 |
| 6,179,781 B1 * | 1/2001 | Phillips | 600/454 |
| 2005/0090747 A1 | 4/2005 | Clark | |

FOREIGN PATENT DOCUMENTS

CN   1440726   9/2003

* cited by examiner

*Primary Examiner* — Tse Chen
*Assistant Examiner* — Patricia Park
(74) *Attorney, Agent, or Firm* — Kory D. Christensen; Stoel Rives LLP

(57) ABSTRACT

The present application provides a method for generating dealiased Doppler signals in a spectral Doppler system. The method comprises the steps of: filtering each of two quadrature components of obtained quadrature Doppler signals by using at least four filters in at least four parallel branches respectively so as to output eight signals, wherein the at least four filters for each quadrature component are equally divided into two groups, and outputs of each group of the filters are to be used for Doppler signals processing in one of forward and reverse directions, and coefficients of the different filters in each group can be interleaved with each other to form coefficients of a desired filter; interleaving and accumulating the output eight dealiased signals, according to direction and quadrature component of the output Doppler signals, to obtain forward and reverse dealiased Doppler signals $F(t)$ and $R(t)$.

22 Claims, 8 Drawing Sheets

ULTRASOUND DOPPLER DEALIASING WITHOUT ZERO INSERTION

RELATED APPLICATION DATA

This application claims priority to Chinese Patent Application No. 200610063140.9, filed on Oct. 13, 2006, the entire disclosure of which is expressly incorporated by reference herein.

FIELD

The present application relates to spectral Doppler technique, more particularly to a method and apparatus for generating dealiased Doppler audio signals.

BACKGROUND

The spectral Doppler technique has been widely applied to noninvasive detection and measurement, especially to the detection and measurement of blood flow in a blood vessel.

In ultrasonic Doppler system, ultrasonic signals are transmitted into a target area of a human body. The transmitted ultrasonic signals are then scattered by the cells of body tissue or those of blood flow in the target area. Part of the scattered signals return back to a receiver of the system, and are converted into electric signals, which are called echo signals. The received echo signals are amplified by an amplifier and analyzed by a series of Doppler processes, to obtain a spectrogram of Doppler signals and valuable indices, such as the velocity of blood flow, for clinic diagnosis.

FIG. 1 is a block diagram of a typical ultrasonic Doppler system. As shown in FIG. 1, the received echo signals are beam-formed and quadrature demodulated to obtain the quadrature Doppler signals. In an ultrasonic Doppler system, the amplitude of the echo signals from the tissue or vascular wall is normally much higher than those from blood flow. For this reason, a high-pass filter (or known as wall filter) is needed to process the obtained quadrature Doppler signals after gap filling. In this way, most of the echo signals from the stationary or near-stationary tissue and vascular wall, which are characterized in high amplitude and extremely low frequency, can be successfully cancelled.

As shown in FIG. 1, after high-pass filtering, the quadrature Doppler signals, in one path, are fed into a spectral analysis unit to calculate the spectrogram. Then, a parameter calculating unit extracts the mean frequency waveform, maximum frequency waveform and etc. based on the spectrogram, thereby producing some valuable indices for clinic use. The spectrogram and the indices, such as the maximum frequency waveform and etc., are then converted by a DSC (Digital Scan Converter) and sent to a monitor for real time display. In the other path, the filtered quadrature Doppler signals are fed into a direction separating unit, where the Doppler signals are separated into forward and reverse components (hereafter referred to as forward and reverse Doppler signals), each of which corresponds to one of the blood flow directions. At last, the separated forward and reverse Doppler signals are converted by a DAC (digital-analog converter) and output to the right and left stereo speakers respectively, so as to output the audio Doppler signals. By using such a Doppler system, doctors can make more accurate diagnosis under the help of the spectrogram displayed in the monitor and the sound from the speaker.

In a spectrogram, the number of frequency points in each spectral line is limited, for example, only 128 points. To obtain the maximum frequency waveform and the mean frequency waveform with high accuracy, the spectrogram is required to fully fill the whole display area. In practical, the velocities of forward and reverse blood flow are usually asymmetrical, and as a result, for example, the bandwidth of forward Doppler signals is double of that for the reverse Doppler signals. In this case, if the spectrogram is still required to fully fill the whole display area, spectral alias will be occurred, that is, the frequency components of the forward Doppler signals will be displayed in the negative frequency range, or vice versa, as shown in FIG. 2. In FIG. 2, the area filled with dots indicates the frequency components of the reverse Doppler signals, and the blank one indicates that of the forward Doppler signals. As shown in FIG. 2, part of the forward Doppler signals are displayed in the negative frequency range of $-\pi \sim 0$, that is, the forward Doppler signals are aliased. FIG. 10a shows the aliasing phenomena in an actual spectrogram. The spectral alias as shown in FIG. 2 will be more obvious in a pulsed wave (PW) Doppler system with low pulse repetition frequency (PRF). In a PW Doppler system, the PRF is usually required to satisfy the following condition:

$$V_{range} < (PRF*c)/(2*f_0)$$

Where $V_{range}$ is the sum of the maximum velocities of forward and reverse blood flow; c is the sound speed, and $f_0$ is the frequency of the transmitted ultrasound wave. If the velocity of blood flow and PRF meets the above condition, the aliasing phenomena may be cancelled, by adjusting the baseline position of a spectrogram during spectral analysis and causing frequency components of the forward and reverse Doppler signals fully fill the whole display area. The adjustment of baseline position may be implemented directly by moving the frequency spectrum of Doppler signals in frequency domain, or by performing digital frequency modulation on Doppler signals in time domain.

Referring back to FIG. 1, after spectral analysis, the Doppler signals are fed into direction separating unit to obtain the forward and reverse Doppler signals. FIG. 3 shows a typical direction separating unit. As shown in FIG. 3, one quadrature component of Doppler signals, i.e. I(t) is filtered by a Hilbert transform filter, and the other quadrature component Q(t) is delayed by a delayer. Then, the filtered I(t) and delayed Q(t) are added up to obtain the reverse Doppler signals R(t), or performed subtraction to obtain the forward Doppler signals F(t). Since the baseline adjustment in a spectrogram will cause the bandwidth in one frequency direction (positive or negative) greater than PRF/2, the output audio Doppler signals will be distorted if the sampling rate thereof still remains PRF. In order to avoid audio distortion and output dealiased forward blood flow signals, the sampling rate of the output audio Doppler signals has to be increased. For example, the maximum sampling rate of output audio Doppler signals is required to be 2 PRF, for the adjustment of baseline position is up to PRF/2.

U.S. Pat. Nos. 5,553,621 and 5,676,148 disclose some methods for generating dealiased Doppler signals without increasing PRF. FIG. 4 illustrates the disclosed method of U.S. Pat. No. 5,553,621. As shown in FIG. 4, the complex signals I(t)+iQ(t), which consists of two quadrature components of Doppler signals, are up-sampled by being inserted zero between two adjacent samples, so that a complex sequence with doubled sampling rate is obtained. The obtained complex sequence is then digitally modulated so as to allow the band center frequency of forward (or reverse) Doppler signals to be zero frequency. The modulated sequence is then filtered by using a low-pass filter with real coefficients, so as to remove the interference caused by the zero insertion. Next, the filtered sequence is demodulated to restore its frequency characteristic. At last, the operation of Re{.} shown in FIG. 4 will be performed on the demodulated complex sequence to acquire real part of the complex sequence, which is the dealiased forward (or reverse) Doppler signals, or called forward (or reverse) blood flow signals.

However, the above method has the following shortcomings: since the zero insertion is performed on the input signals, the computation amount and the desired memory space during audio signals processing will be increased significantly, which results in high cost and lower practicability. In addition, the above method needs to obtain the analytic signals (single side band signals) of unidirectional (forward or reverse) blood flow signals first, and then output the real part of the analytic signals. This increases the complexity of processing.

Moreover, US2005/0090747 also provides a method for generating dealiased Doppler signals, but without up-sampling processing. That is, the Doppler system determines the aliased frequency points based on the detected maximum frequency, and then automatically performs frequency modulation on the input signals. The drawback of this method is that: the modulated signals may be distorted, since the sampling rate of the output signals are same as that of input ones.

SUMMARY

An object is to provide a method and apparatus for processing Doppler signals, so as to generate dealiased Doppler signals without distortion and reduce the computation amount and complexity.

According to one aspect, a method for generating dealiased Doppler signals in a spectral Doppler system is provided. The method comprises the steps of:

filtering each of two quadrature components of obtained quadrature Doppler signals by using at least four filters in at least four parallel branches respectively so as to output eight signals, wherein the at least four filters for each quadrature component are equally divided into two groups, and outputs of each group of the filters are to be used for Doppler signals processing in one of forward and reverse directions, and coefficients of the different filters in each group can be interleaved with each other to form coefficients of a desired filter;

Interleaving and accumulating the output eight signals, according to directions and quadrature component of the output Doppler signals, to obtain forward and reverse dealiased Doppler signals F (t) and R (t).

According to another aspect, a dealiasing apparatus used in a spectral Doppler system is provided for performing the above method.

According to still another aspect, a dealiasing apparatus used in a spectral Doppler system is provided. The dealiasing apparatus comprises: four first filters, for filtering one of two quadrature components of obtained quadrature Doppler signals in parallel, to output four signals;

four second filters, for filtering the other quadrature component of the quadrature Doppler signals in parallel to output four signals;

wherein the four filters for each quadrature component are equally divided into two groups, and outputs of each group of the filters are to be used for Doppler signals processing in one of forward and reverse directions, and coefficients of the two different filters in each group can be interleaved with each other to form coefficients of a desired filter;

an interleaving and accumulating unit, for interleaving and accumulating the eight signals, according to direction and quadrature component of the output Doppler signals, so as to obtain forward and reverse dealiased Doppler signals F(t) and R(t).

The schemes provided herein may directly filter quadrature Doppler signals I(t) and Q(t) without zero insertion, and separate the filtered signals into forward and reverse Doppler signals without distortion and alias. Therefore, the schemes can reduce the complexity and computation amount, and thereby the Doppler system may be implemented in real time with low cost and high efficiency.

Other objects and attainments will become apparent and appreciated by referring to the following description and claims taken in conjunction with the accompanying drawings.

DETAILED DESCRIPTION

The preferred embodiments will be described below in conjunction with the appended drawings.

The present embodiment(s) is provided based on a multirate structure of digital filter. For solving the problems in the prior art, such as the large amount of computation in the zero insertion and filtering method, it is provided that: the quadrature Doppler signals are directly filtered by a plurality of filters (for example, 4 filters for each quadrature component) in parallel to obtain dealiased signals, and then the filtered signals are interleaved and accumulated to obtain forward and reverse dealiased Doppler signals.

Figure 5:
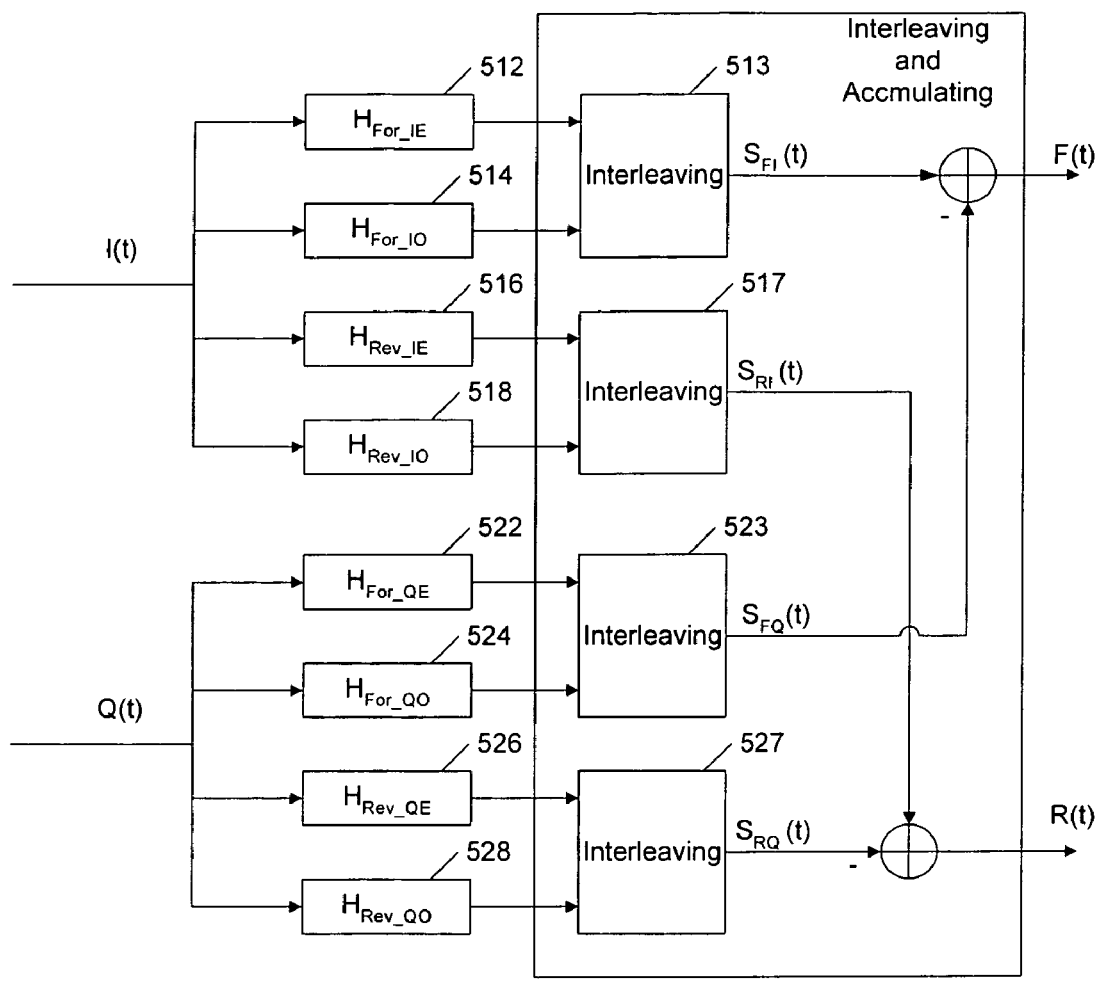
FIG. 5 is a block diagram for showing the structure of a dealiasing apparatus in a Doppler system according to an embodiment.

FIG. 5 shows a block diagram of an apparatus for generating dealiased Doppler signals according to an embodiment.

As shown in FIG. 5, each quadrature component of the quadrature Doppler signals is filtered by four filters. For example, the original input quadrature component I (t) is first filtered by four filters 512, 514, 516 and 518, in four parallel branches at the same time. The transfer functions of the four filters are $H_{For\_IE}$, $H_{For\_IO}$, $H_{Rev\_IE}$, and $H_{Rev\_IO}$ respectively. Wherein, from the transfer functions of the filters, it can be seen that the four filters may be divided into two groups. One group includes filters 512 and 514, which output the signals to be processed for obtaining forward Doppler signals. The other group includes filters 516 and 518, which output the signals to be processed for obtaining reverse Doppler signals. Furthermore, the filter coefficients of two filters included in the same group (for example, filters 512 and 514) may be interleaved with each other to form the coefficients of a desired filter. In present embodiment, the desired filter is equivalent to the one whose output is processed to obtain Doppler signals in the same direction (forward or reverse) in the zero insertion and filtering method. Also, the coefficients of two filters in one group may be the even and odd index series of the desired filter's coefficients respectively, and thereby each transfer function may be identified by a subscript of E (even) or O (odd). The method of designing the coefficients of the desired filter and individual filters 512, 514, 516 and 518 will be described later in connection with FIGS. 6-8.

Similarly, the quadrature component Q(t) of Doppler signals is filtered by four filters 522, 524, 526 and 528, in four parallel branches at the same time. The transfer functions of the four filters are $H_{For\_QE}$, $H_{For\_QO}$, $H_{Rev\_QE}$, and $H_{Rev\_QO}$ respectively. The processing performed by these filters is same as that for I(t), and thus detailed description thereof is omitted here.

For the quadrature component I(t), the outputs of two filters in the same group (e.g. filters 512 and 514, or filters 516 and 518) are then fed into an interleaving unit (e.g. 513 or 517). Each of the interleaving units (e.g. 513) merges the outputs of the two filters 512 and 514 into one sequence, in which, for example, the even index sequence are come from one filter's outputs and the odd index sequence are come from the other filter's outputs. In this way, the interleaved signals $S_{FI}(t)$ and $S_{RI}(t)$ are obtained in the two groups for quadrature component I(t). Wherein, $S_{FI}(t)$ and $S_{RI}(t)$ will be processed to obtain the forward and reverse dealiased Doppler signals, and thereby each of the signals is identified by a subscript of F(forward) or R(reverse). The same processing may be performed on quadrature component Q(t) to obtain the interleaved signals $S_{FQ}(t)$ and $S_{RQ}(t)$. Up to now, the four signals $S_{FI}(t)$, $S_{RI}(t)$, $S_{FQ}(t)$ and $S_{RQ}(t)$ are obtained by filtering and interleaving.

Figure 1:
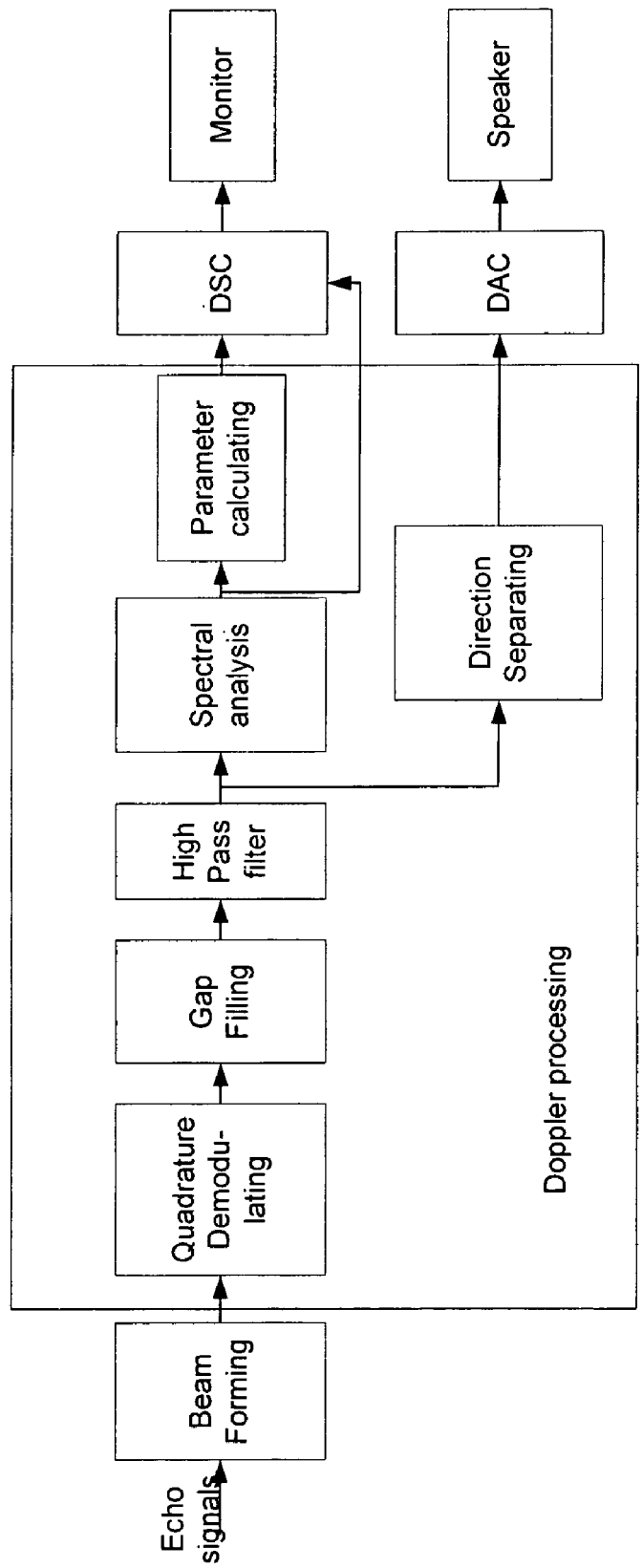
FIG. 1 is a block diagram of a typical ultrasonic Doppler system.

Among the signals $S_{FI}(t)$, $S_{RI}(t)$, $S_{FQ}(t)$ and $S_{RQ}(t)$, those corresponding to the Doppler signals processing in the same direction but from the different quadrature components, are accumulated as shown in FIG. 5. Specifically, the signals $S_{FI}(t)$ and $S_{FQ}(t)$; which correspond to Doppler signals processing in forward direction but from different quadrature components I(t) and Q(t), are accumulated to generate the forward dealiased Doppler signals, or called forward blood flow signals F(t). Similarly, $S_{RI}(t)$ and $S_{RQ}(t)$ are accumulated as shown in FIG. 5 to generate the reverse dealiased Doppler signals, or called reverse blood flow signals R(t). In this way, the speaker of FIG. 1 may output the forward and reverse blood flow signals without any distortion and alias.

The structure of the apparatus and the processing procedure thereof have been described as above in connection with FIG. 5. In the structure of FIG. 5, designing the coefficients of the desired filters and individual filters is one of critical and challenging steps. As described above, in the present embodiment, the desired filter may be equivalent to the corresponding one used in the zero insertion and filtering method. Therefore, in order to obtain the coefficients of each filter in FIG. 5, it is required to design a zero insertion and filtering structure that is equivalent to the structure of FIG. 5, and obtain the coefficients of the desired filters.

The method of designing the desired filters will be described below in connection with FIGS. 6-8.

Figure 6:
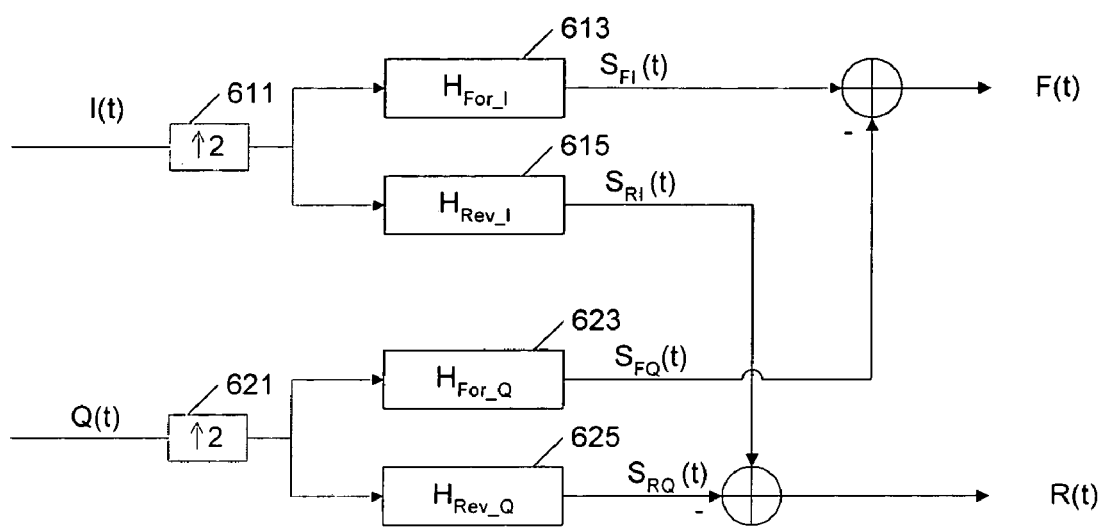
FIG. 6 shows an apparatus for generating dealiased Doppler signals that is a basis of an embodiment.

FIG. 6 shows an apparatus for generating dealiased Doppler signals by using the zero insertion and filtering method, which is equivalent to that of FIG. 5.

Figure 2:
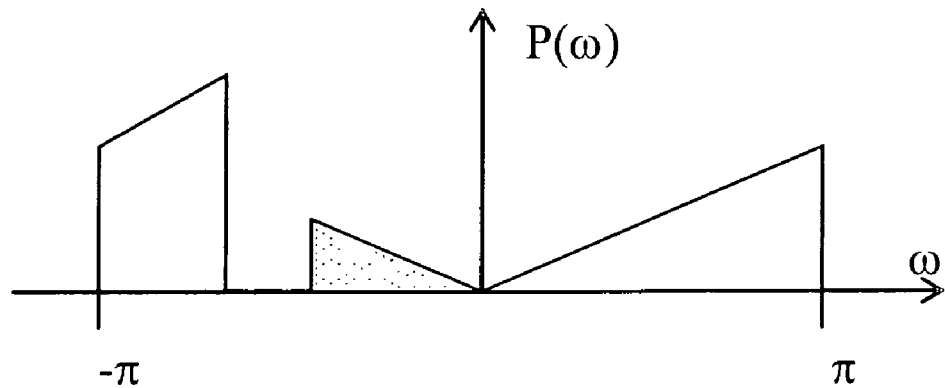
FIG. 2 illustrates the aliasing phenomena occurred in typical Doppler system.
Figure 3:
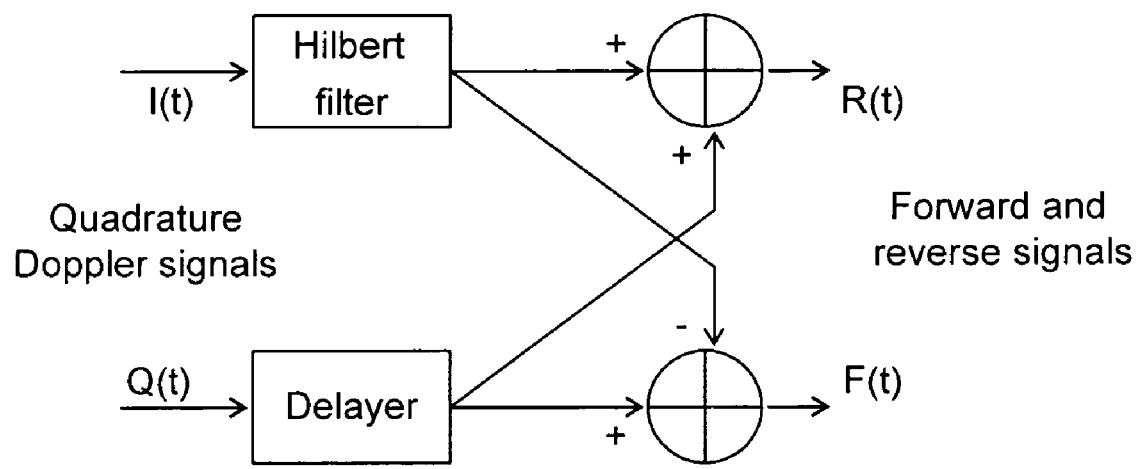
FIG. 3 is a block diagram for showing the structure of a typical direction separating unit.
Figure 4:
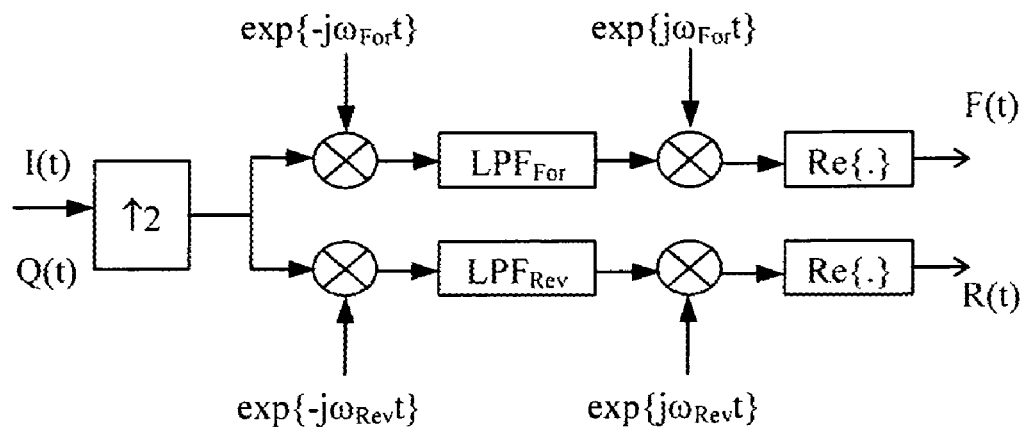
FIG. 4 illustrates a dealiasing apparatus in prior art.

As shown in FIG. 6, the input quadrature component of Doppler signals, for example I(t) (given that the input quadrature Doppler signals have the frequency characteristic of FIG. 2) is up-sampled by zero insertion in unit 611. The up-sampled signals have the frequency characteristic of FIG. 7. As shown in FIG. 7, after being up-sampled, the signals' frequency spectrum is copied in the frequency range of $-\pi\sim\pi$, in other words, it is compressed into half of the original one. The up-sampled signals of I(t) are then filtered in parallel by two FIR(finite impulse response) filters 613 and 615, to obtain signals $S_{FI}(t)$ and $S_{RI}(t)$. The transfer functions of the two filters 613 and 615 may be expressed as $H_{For\_I}$, $H_{Rev\_I}$. As shown in FIG. 6, the same processing may be performed on Q(t), that is, after being up-sampled by unit 621, Q(t) is filtered in parallel by two filters 623 and 625, to obtain $S_{FQ}(t)$ and $S_{RQ}(t)$. The transfer functions of the two filters 623 and 625 may be expressed as $H_{For\_Q}$, $H_{Rev\_Q}$. Comparing FIG. 5 with FIG. 6, it can be seen that the signals $S_{FI}(t)$, $S_{RI}(t)$, $S_{FQ}(t)$ and $S_{RQ}(t)$, obtained by using zero insertion and filtering method, are the same signals as those expected to be obtained in present embodiment. Thus, in the same way as FIG. 5, the obtained signals, which correspond to the Doppler signals processing in the same direction but from different quadrature components I(t) and Q(t), are accumulated to generate the forward or reverse dealiased Doppler signals. In specific, the signals $S_{FI}(t)$ and $S_{FQ}(t)$ are accumulated to generate the forward dealiased Doppler signals F(t), while $S_{RI}(t)$ and $S_{RQ}(t)$ are accumulated to generate reverse dealiased Doppler signals R(t).

Comparing FIG. 5 and 6, it can be seen that filters $H_{For\_I}$, $H_{Rev\_I}$ and $H_{For\_Q}$, $H_{Rev\_Q}$ of FIG. 6 correspond to different quadrature components and are used for Doppler signals processing in different directions (forward and reverse), in other words, they correspond to the groups of the filters of FIG. 5. Thus, $H_{For\_I}$, $H_{Rev\_I}$ and $H_{For\_Q}$, $H_{Rev\_Q}$ may be the desired filters of the embodiment shown in FIG. 5. How to obtain the coefficients of desired filters will be given in following.

In FIG. 6, in order to obtain forward and reverse Doppler signals without any distortion, the filters $H_{For\_I}$ and $H_{For\_Q}$ (i.e. units 613 and 623) should have the same amplitude-frequency response, and their phase-frequency responses should have 90° phase difference from each other. Similarly, the filters $H_{Rev\_I}$ and $H_{Rev\_Q}$ (units 615 and 625) should have the same amplitude-frequency response, and their phase-frequency responses should have 90° phase difference from each other. In this way, the filters $H_{For\_I}$ and $H_{For\_Q}$ (units 613 and 623) may form a complex coefficient filter $H_{For\_I}+i*H_{For\_Q}$, whose frequency response is nonzero only in the frequency range corresponding to forward Doppler signals, that is, it is valid in the range of $0\sim\pi$. In the other words, the complex coefficient filter is used to select forward Doppler signals. In the same way, the filters $H_{Rev\_I}$ and $H_{Rev\_Q}$ (units 615 and 625) may form a complex coefficient filter $H_{Rev\_I}+i*H_{Rev\_Q}$, whose frequency response is nonzero only in the frequency range corresponding to reverse Doppler signals, that is, it is valid in the range of $-\pi\sim0$. That is, this complex coefficient filter is used to select reverse Doppler signals. The frequency responses of the above two complex coefficient FIR filters are shown in FIG. 8, and indicated by bold line with transfer functions $H_{For}(\omega)$ and $H_{Rev}(\omega)$ respectively.

In Digital filter processing, the FIR filter performs convolution operation on the input signals and the filter coefficients. For example, the outputs of the complex coefficient filter $H_{For\_I}+i*H_{For\_Q}$, which is used to select forward Doppler signals, may be expressed as:

$$F'(t) = [I(t) + iQ(t)] \otimes [H_{For\_I}(t) + iH_{For\_Q}(t)]$$
$$= [I(t) \otimes H_{For\_I}(t) - Q(t) \otimes H_{For\_Q}(t)] +$$
$$i[I(t) \otimes H_{For\_Q}(t) + Q(t) \otimes H_{For\_I}(t)]$$

Where, $\otimes$ indicates the convolution operation. Then, obtain the real part of the output complex sequence, i.e. the forward dealiased Doppler signals, which may be expressed as:

$$F(t) = I(t) \otimes H_{For\_I}(t) - Q(t) \otimes H_{For\_Q}(t)$$

Based on above, it is apparent that, by filtering I(t) and Q(t) with the two complex coefficient filters and accumulating the filtered signals correspond to the same direction, the forward or reverse Doppler signals may be obtained.

Here, the complex coefficient filter $H_{For\_I} + i^*H_{For\_Q}$ may be obtained by designing a low-pass filter $H_{For}$ and multiplying the $H_{For}$ by a complex sine wave. In the same way, the complex coefficient filter $H_{Rev\_I} + i^*H_{Rev\_Q}$ may be obtained by designing a low-pass filter $H_{Rev}$ and multiplying the $H_{Rev}$ by a complex sine wave. The cutoff frequency of the designed low-pass filter and the frequency of the sine wave are related to the baseline position in a spectrogram, the details are shown as follows.

First, suppose that a spectrogram to be displayed meets the following requirements: the spectrogram has 256 frequency points; the original baseline position is at the 128$^{th}$ frequency point; the 0th frequency point may be denoted as a digital angle frequency $\omega = -\pi$; and the 255$^{th}$ frequency point is $\omega = 127\pi/128$. Then, the cutoff frequency $fc_F$ and $fc_R$ of the low-pass filters $H_{For}$ and $H_{Rev}$ may be expressed as:

$$fc_F = 0.125 - \frac{K_{base}}{256*4}$$
$$fc_R = 0.125 + \frac{K_{base}}{256*4}$$

Where $K_{base}$ is the number of points by which the baseline is moved. If the baseline is moved by 32 points along a positive frequency direction, then the 160th point corresponds to zero frequency. In this case, the bandwidth of forward Doppler signals is $0.75\pi$ in spectrogram, and that of reverse Doppler signals is $1.25\pi$. It should be noted that: for the signals that are up-sampled by zero insertion, the signals' bandwidth is only half of the original one, further the low-pass filter has symmetric frequency response in positive and negative frequency area. Thus, the low-pass filter designed as above only have the bandwidth of $0.25\pi$, that is, $fc_F$ and $fc_R$ are $0.1875\pi$ and $0.31257\pi$ respectively, and corresponding normalized frequencies are 0.09375 and 0.15625. The results are same as those obtained by substituting the number of moved points 32 for Kbase in the above equations. Correspondingly, the frequency of complex sine wave for modulating may be selected as $fc_F$ and $-fc_R$.

By using the designing method as described above, the complex coefficient filters can be obtained, and expressed as:

$$H_{For\_IQ} = H_{For}*\exp(i*2*pi*fc_F) = H_{For\_I} + i^*H_{For\_Q},$$
and
$$H_{Rev\_IQ} = H_{Rev}*\exp(-i*2*pi*fc_R) = H_{Rev\_I} + i^*H_{RevQ}$$

Figure 8:
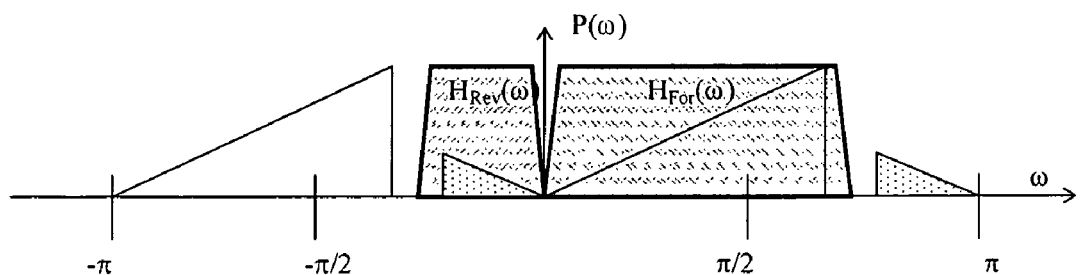
FIG. 8 shows the frequency response of a complex coefficient filter for selecting forward and reverse Doppler signals.

And their frequency responses are same as those shown in FIG. 8.

Figure 7:
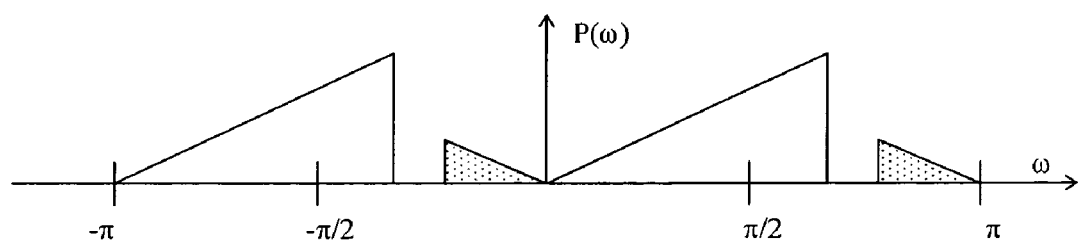
FIG. 7 shows the frequency spectrum of signals up-sampled by zero insertion.

Through the method descried above in conjunction with FIGS. 6-8, the desired filters' coefficients of FIG. 5 may be obtained. According to the inventive concept, the coefficients of individual filters of FIG. 5 may be calculated from those of desired filters.

For example, the coefficients of FIR filters 512 and 514 ($H_{For\_IE}$ and $H_{For\_IO}$) in FIG. 5 may be the even and odd index series of the coefficients for FIR filter 613 ($H_{For\_I}$) in FIG. 6 respectively. In FIG. 5, the coefficients of FIR filters 516 and 518 ($H_{Rev\_IE}$ and $H_{Rev\_IO}$) may also be the even and odd index series of the coefficients for FIR filter 615 ($H_{Rev\_I}$) in FIG. 6, respectively. In the same way, the coefficients of the four filters for Q(t) may be obtained from those of filters 623 and 625 in FIG. 6.

Alternatively, the coefficients of individual FIR filters in FIG. 5 may be calculated directly from the pre-designed complex coefficient filters $H_{For\_IQ}$ and $H_{Rev\_IQ}$. For example, the coefficients of filters 512 and 514 ($H_{For\_IE}$ and $H_{For\_IO}$) may be the even and odd index series of the real coefficients of $H_{For\_IQ}$, respectively; the coefficients of filters 522 and 524 ($H_{For\_QE}$ and $H_{For\_QO}$) may be the even and odd index series of the imaginary coefficients for $H_{For\_IQ}$, respectively. In the same way, the coefficients of the filters 516, 518, 526 and 528 for the Doppler signals processing in reverse direction may be obtained from the complex coefficient filter $H_{Rev\_IQ}$.

As described above, the coefficients of all of the filters in FIG. 5 can be determined. Subsequently, as shown in FIG. 5, these well-designed filters are used to filter the Doppler signals directly, and then the filtered signals are interleaved and accumulated to obtain the forward and reverse dealiased Doppler signals. By using the structure of FIG. 5, the obtained dealiased Doppler signals may be same as those obtained by using zero insertion and filtering method. Meanwhile, the method is implemented without zero insertion, thereby reducing the cost and computation amount.

Figure 9:
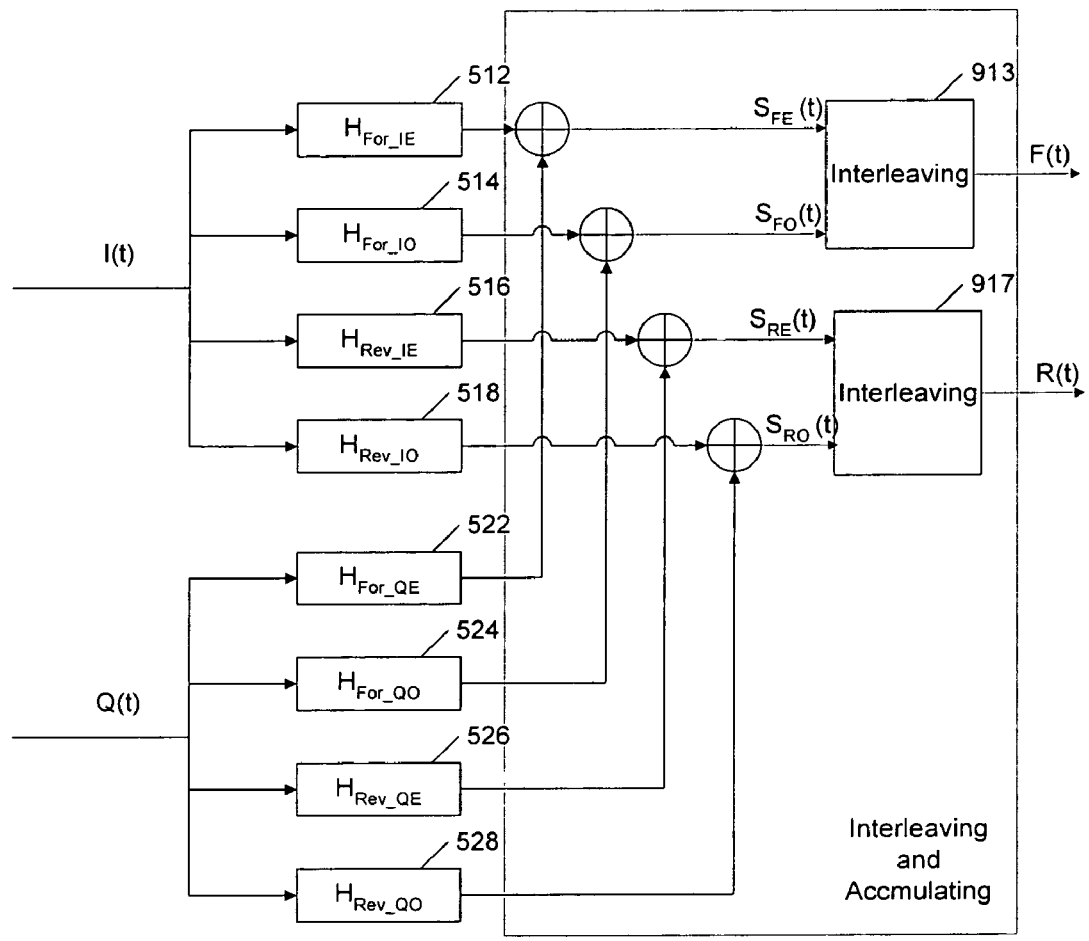
FIG. 9 is a block diagram for showing the structure of a dealiasing apparatus in a Doppler system according to another embodiment.

FIG. 9 shows a block diagram of an apparatus for generating dealiased Doppler signals according to another embodiment. In this embodiment, all of the units except the interleaving units and accumulating unit are same as those in FIG. 5. The same units are identified with same reference number, and the detailed description thereof is omitted.

As shown in FIG. 9, each of the quadrature components of Doppler signals I(t) and Q(t) is filtered in four branches by four filters in parallel, and as a result, filtered signals are output in total 8 branches for I(t) and Q(t). Then, the filtered signals corresponding to different quadrature components are added in one to one manner. For example, the outputs of filter 512($H_{For\_IE}$) may be added to that of filter 522($H_{For\_QE}$) to generate the signals $S_{FE}(t)$; the output of filter 518($H_{Rev\_IO}$) may be added to that of filter 528($H_{Rev\_QO}$) to generate the signals $S_{RO}(t)$. The outputs of other filters may be added up in the same way, so that there are added signals $S_{FE}(t)$, $S_{FO}(t)$, $S_{RE}(t)$ and $S_{RO}(t)$ in four branches. Next, the added signals, which correspond to the Doppler signals processing in the same direction, are interleaved with each other to form one sequence. In one interleaved sequence, for example, the even index sequence comes from $S_{FE}(t)$ and the odd index sequence comes from $S_{FO}(t)$, thus the interleaved sequence is forward Doppler signals F(t). Similarly, $S_{RE}(t)$ and $S_{RO}(t)$ are interleaved with each other to form the reverse Doppler signals R(t).

Two embodiments have been described in detail as above. However, the present invention is not limited to above embodiments. Although the both embodiments utilize 4 filters to process each quadrature component of Doppler signals, the system may use more than 4 filters to process each quadrature component according to the practical requirements. For example, in the case of implementing the filters in hardware, a number of multipliers, adders and delaying registers may be needed to realize the filter, wherein the multiplier may consume a large amount of resource. In this case, the filters in above embodiments may be further split into several filters with short coefficients. By increasing the frequency of a calculation clock, the several split filters may be implemented in time-division multiplexing manner, and then the outputs of the split filters may be accumulated to obtain the results equivalent to a single one with long coefficients. Such a solution may save the hardware resource.

In addition, the method for generating dealiased Doppler signals is not limited to the application in an ultrasonic Doppler system, but also may be applied to other kind of spectral Doppler systems for removing the aliased Doppler signals.

The dealiasing apparatus as described above may be implemented in hardware, such as FPGA (Field Programmable Gate-Array) or ASIC (Application Specific Integrate Circuit), for real time processing in embedded system with lower cost. Additionally, the method of generating the dealiased Doppler signals as illustrated in conjunction with drawings may be implemented as a software, the flow chat of which may follow the processing procedure as described above.

The Advantageous Effect

In the dealiasing method and apparatus provided herein, the quadrature Doppler signals I(t) and Q(t) may be directly filtered without zero insertion, and may be directly processed to obtain the forward and reverse Doppler signals without modulation and demodulation. Therefore, the method and apparatus may reduce the cost and computation amount, and avoid the output signals from distortion.

Figure 10A:
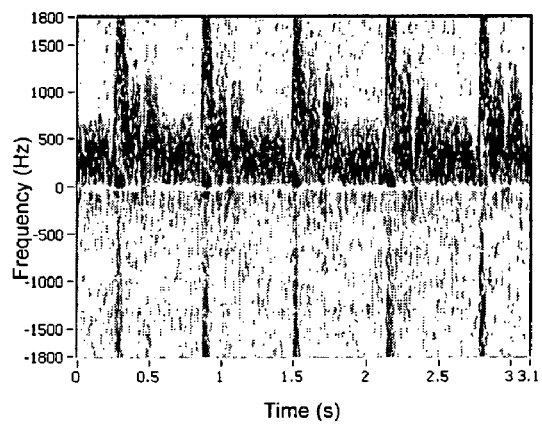
FIG. 10a-10c illustrates the experiment results
Figure 10B:
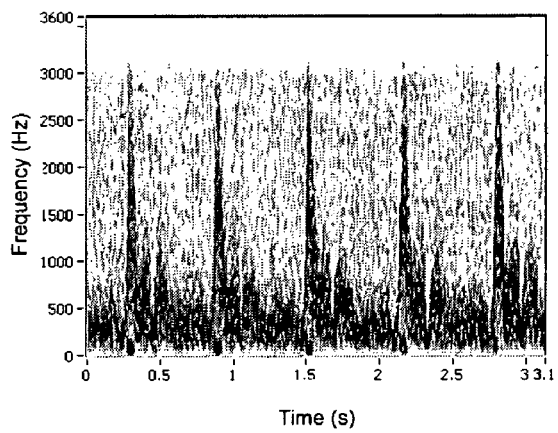
Figure 10C:
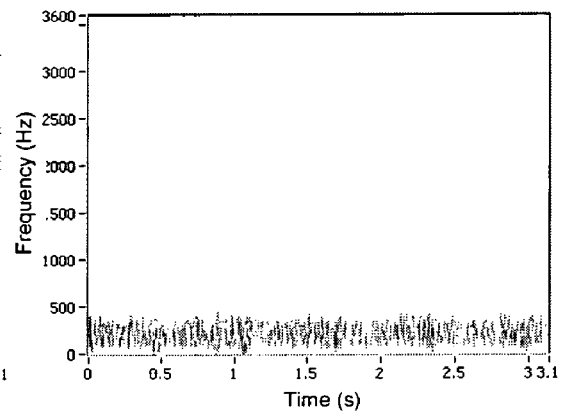

FIGS. 10a-10c show the experiment results obtained by using the method and apparatus. FIG. 10a shows the spectrogram of signals before filtering, wherein the sampling rate of quadrature Doppler signals is 3.6 KHz. As shown in FIG. 10a, the alias phenomena is obvious in bidirectional spectrum, that is, the frequency components of forward Doppler signals are aliased in negative frequency range. After being processed by using the method described herein, the spectrogram of forward and reverse Doppler signals are shown in FIGS. 10b and 10c, respectively. FIGS. 10b and 10c illustrate two real Doppler signals in a single frequency direction (since the real Doppler signals have symmetric frequency characteristic in positive and negative frequency range, only the positive part of the spectrum is shown here). From the figures, it can be seen that the processed signals have increased sampling rate up to 7.2 KHz, and there is no aliased frequency component for forward Doppler signals in the negative frequency range.

What is claimed is:

1. A method for generating dealiased Doppler signals in a medical ultrasound spectral Doppler system, comprising the steps of:
    directly filtering each of two separated baseband quadrature components of obtained quadrature Doppler signals without zero insertion by using at least four filters in at least four parallel branches respectively so as to output eight signals, wherein the at least four filters for each separated baseband quadrature component are equally divided into two groups, and outputs of each group of the filters are to be used for Doppler signals processing in one of forward and reverse directions, and coefficients of the different filters in each group can be interleaved with each other to form coefficients of a desired filter;
    interleaving and accumulating the output eight signals, according to direction and quadrature component of the output Doppler signals, to obtain forward and reverse dealiased Doppler signals F(t) and R(t).

2. The method of claim 1, wherein two of the desired filters, which correspond to different quadrature components but to the Doppler signals processing in the same direction, have the same amplitude-frequency response, but their phase-frequency responses have 90° phase difference from each other.

3. The method of claim 2, wherein the coefficients of the two desired filters are respectively real part and imaginary part of complex coefficients of a pre-designed complex coefficient filter, which is used for selecting one of the forward and reverse dealiased Doppler signals.

4. The method of claim 3, wherein the complex coefficient filter is obtained by multiplying a low-pass filter by a complex sine wave having a predetermined frequency.

5. The method of claim 4, wherein the low-pass filter's cutoff frequency and the predetermined frequency of the complex sine wave are related to baseline position in a spectrogram.

6. The method of claim 1, wherein the each group includes at least two filters, and the coefficients of the two filters are respectively even and odd index series of the coefficients of the desired filter.

7. The method of claim 1, wherein the step of interleaving and accumulating comprises:
    interleaving outputs of at least two filters in each group for each quadrature component,
    accumulating the interleaved signals that correspond to different quadrature components but to the Doppler signals processing in the same direction, so as to obtain the forward and reverse dealiased Doppler signals F(t) and R(t).

8. The method of claim 1, wherein the step of interleaving and accumulating comprises:
    accumulating outputs of the individual filters for different quadrature components in one to one manner, to obtain accumulated signals in at least four branches;
    interleaving the accumulated signals for the Doppler signals processing in the same direction, to obtain the forward and reverse dealiased Doppler signals F(t) and R(t).

9. The method of claim 1, wherein the desired filter is a pre-designed filter for filtering up-sampled Doppler signals, to obtain the dealiased Doppler signals.

10. A dealiasing apparatus in a medical ultrasound spectral Doppler system, comprising:
    at least four first filters, configured to directly filter one of two separated baseband quadrature components of obtained quadrature Doppler signals without zero insertion in parallel to output at least four signals;
    at least four second filters, configured to filter the other separated baseband quadrature component of the quadrature Doppler signals to output at least four signals;
    wherein the at least four filters for each separated baseband quadrature component are equally divided into two groups, and outputs of each group of the filters are to be used for Doppler signals processing in one of forward and reverse directions, and coefficients of different filters in each group configured to be interleaved with each other to form coefficients of a desired filter;
    an interleaving and accumulating unit, configured to interleave and accumulate the at least eight signals, according to direction and quadrature component of the output Doppler signals, to obtain forward and reverse dealiased Doppler signals F(t) and R(t).

11. The apparatus of claim 10, wherein two of the desired filters, which correspond to different quadrature components but to the Doppler signals processing in the same direction, have the same amplitude-frequency response, but their phase-frequency responses have 90° phase difference from each other.

12. The apparatus of claim 11, wherein the coefficients of the two desired filter are respectively real part and imaginary part of complex coefficients of a pre-designed complex coefficient filter, which is used for selecting the one of the forward and reverse dealiased Doppler signals.

13. The apparatus of claim 12, wherein the complex coefficient filter is obtained by multiplying a low-pass filter by a complex sine wave having a predetermined frequency.

14. The apparatus of claim 13, wherein the low-pass filter's cutoff frequency and the predetermined frequency of the complex since wave are related to baseline position in a spectrogram.

15. The apparatus of claim 10, wherein the each group includes at least two filters, and the coefficients of the two filters are respectively even and odd index series of the coefficients of the desired filter.

16. The apparatus of claim 10, wherein the interleaving and accumulating unit comprises:
an interleaving unit, configured to interleave the outputs of the at least two filters in each group for each quadrature component,
an accumulating unit, configured to accumulate the interleaved signals that correspond to different quadrature components but to the Doppler signals processing in the same direction, so as to obtain the forward and reverse dealiased Doppler signals F(t) and R(t).

17. The apparatus of claim 10, wherein the interleaving and accumulating unit comprises:
an accumulating unit, configured to accumulate the outputs of the individual filters for different quadrature components in one to one manner, to obtain accumulated signals in at least four branches;
an interleaving unit, configured to interleave the accumulated signals for the Doppler signals processing in the same direction, to obtain the forward and reverse dealiased Doppler signals F(t) and R(t).

18. The apparatus of claim 10, wherein the desired filter is a pre-designed filter configured to filter up-sampled Doppler signals, to obtain the dealiased Doppler signals.

19. A dealiasing apparatus in a medical ultrasound spectral Doppler system, comprising:
four first filters, configured to directly filter one of two separated baseband quadrature components of obtained quadrature Doppler signals without zero insertion in parallel, to output four signals;
four second filters, configured to filter the other separated baseband quadrature component of the quadrature Doppler signals in parallel to output four signals;
wherein the four filters for each separated baseband quadrature component are equally divided into two groups, and outputs of each group of the filters are to be used for Doppler signals processing in one of forward and reverse directions, and coefficients of the two different filters in each group configured to be interleaved with each other to form coefficients of a desired filter;
an interleaving and accumulating unit, configured to interleave and accumulate the eight dealiased signals, according to direction and quadrature component of the output Doppler signals, so as to obtain forward and reverse dealiased Doppler signals F(t) and R(t).

20. The apparatus of claim 19, wherein the interleaving and accumulating unit comprises:
an interleaving unit, configured to interleave the outputs of the two filters in each group for each quadrature component,
an accumulating unit, configured to accumulate the interleaved signals that correspond to different quadrature components but to the Doppler signals processing in the same direction, so as to obtain the forward and reverse dealiased Doppler signals F(t) and R(t).

21. The apparatus of claim 19, wherein the interleaving and accumulating unit comprises:
an accumulating unit, configured to accumulate the outputs of the individual filters for different quadrature components in one to one manner, to obtain accumulated signals in four branches;
an interleaving unit, configured to interleave the accumulated signals for the Doppler signals processing in the same direction, to obtain the forward and reverse dealiased Doppler signals F(t) and R(t).

22. The apparatus of claim 19, wherein the desired filter is a pre-designed filter configured to filter up-sampled Doppler signals, to obtain the dealiased Doppler signals, and two of the desired filter, which correspond to different quadrature components but to the Doppler signals processing in the same direction, respectively have the same coefficients as real part and imaginary part of complex coefficients of a pre-designed complex coefficient filter, which is used for selecting one of the forward and reverse dealiased Doppler signals.

* * * * *